(12) United States Patent
Susa et al.

(10) Patent No.: US 6,770,310 B1
(45) Date of Patent: Aug. 3, 2004

US006770310B1

(54) PICKLE SOLUTION INCLUDING TRANSGLUTAMINESE, METHOD OF MAKING AND METHOD OF USING

(75) Inventors: Yasuyuki Susa, Kawasaki (JP); Hiroyuki Nakagoshi, Kawasaki (JP); Shoji Sakaguchi, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 119 days.

(21) Appl. No.: 09/662,844

(22) Filed: Sep. 15, 2000

(30) Foreign Application Priority Data

Sep. 17, 1999 (JP) .......................................... 11-263479

(51) Int. Cl.[7] .......................... A23L 1/314; A23L 1/318
(52) U.S. Cl. ............................. 426/56; 426/58; 426/63; 426/641; 426/652
(58) Field of Search ............................. 426/56, 58, 63, 426/641, 652

(56) References Cited

U.S. PATENT DOCUMENTS

| | | | | |
|---|---|---|---|---|
| 5,518,742 A | * | 5/1996 | Soeda et al. .................... | 426/63 |
| 5,948,662 A | | 9/1999 | Kobayashi et al. .......... | 435/193 |
| 6,303,162 B1 | * | 10/2001 | Susa et al. ..................... | 426/56 |

FOREIGN PATENT DOCUMENTS

| | | |
|---|---|---|
| DE | 198 40 744 | 3/2000 |
| EP | 0 898 895 | 3/1999 |
| EP | 0 963 704 | 12/1999 |
| JP | 7 008225 | 1/1995 |
| JP | 9 299065 | 11/1997 |
| WO | WO 94/21129 | 9/1994 |

OTHER PUBLICATIONS

Guo–Jane Tsai, et al., Journal of Food Science, vol. 61, No. 6, pp. 1234–1238, "Transglutaminase from Streptoverticillium Ladakanum and Application to Minced Fish Product", 1996.

Y. Kumazawa, et al., Journal of Food Science, vol. 60, No. 4, pp. 715–717 and 726, "Suppression of Surimi Gel Setting by Transglutaminase Inhibitors", 1995.

Noriki Nio, et al., Agricultural and Biological Chemistry, vol. 49, No. 8, pp. 2283–2286, "Gelation of Casein and Soybean Globulins by Transglutaminase", 1985.

A. A. Nowsad, et al., Nippon Suisan Gakkaishi, vol. 59, No. 6, pp. 1017–1021, "Effects of Amine Salts on the Elasticity of Suwari Gel from Alaska Pollack", 1993.

Jianrong Wan, et al., Fisheries Science, vol. 61, No. 6, pp. 968–972, "Inhibitory Factors of Transglutaminase in Salted Salmon Meat Paste", 1995.

* cited by examiner

*Primary Examiner*—Arthur L. Corbin
(74) *Attorney, Agent, or Firm*—Oblon, Spivak, McClelland, Maier & Neustadt, P.C.

(57) ABSTRACT

The present invention provides a composition having protein, transglutaminase and a transglutaminase suppressing compound such as an ammonium salt, which is useful in the preparation of pickle solutions and in methods of making processed meat products with the pickle solution.

24 Claims, No Drawings

US 6,770,310 B1

PICKLE SOLUTION INCLUDING TRANSGLUTAMINESE, METHOD OF MAKING AND METHOD OF USING

BACKGROUND OF THE INVENTION

1. Field of the Invention

The present invention relates to a composition which can be used as a salting agent for preparation of processed meat products such as ham, bacon and roast pork where the composition contains transglutaminase and a compound which suppresses the activity of transglutaminase. In addition, the present invention relates to a pickle solution containing the composition wherein the viscosity of a protein-containing pickle does not significantly increase when the transglutaminase is added to the pickle. Therefore, the quality of processed meat products such as ham, bacon and roast pork which are produced with the pickle are significantly improved.

2. Description of Related Art

A curing step for permeating and dispersing a salting agent into raw meat materials is usually required for manufacturing processed meat products such as ham and bacon. These methods include a dry-curing method, a pickle curing method, and a pickle-injection method. The pickle curing method and the pickle-injection method are generally the most effective.

The pickles typically are a solution of a salting agent which is made up of sodium chloride and color-fixing agents. Additionally, polyphosphate and ascorbic acids are added to the pickle to improve the yield, water holding capacity, binding capacity and color-fixing ability and the like. Pickles also often contain seasonings, preservatives and additional color-fixing agents.

Pickles are often blended with various protein materials, e.g, egg white, whey protein, caseins such as sodium casein or soy bean protein, for the purpose of improving water retentivity, emulsification, food taste and texture, e.g., firmness, elasticity and bindability.

In addition, transglutaminase (hereinafter abbreviated as TGase) may be added to improve food taste, food texture and increasing slice yield (sliceability). TGase reacts with proteins in the pickle and with the proteins in the meat when the pickle permeates or is injected into the meat, which remarkably improves the physical properties of the resulting final product Since TGase effect is more pronounced in the presence of higher amounts of protein, the presence of TGase is highly important for pickles containing high amounts of protein materials. However, when TGase is used in increasing amounts with the higher concentrations of protein materials, the viscosity of the resulting pickle significantly increases.

Generally the pickle is left to stand in a low-temperature stock chamber for one to four days after preparation and before use, to insure that any powdery materials including protein materials are fully dissolved and to allow any bubbles or foam which are present to dissipate. TGase is often supplied as a powder and therefore is dissolved into the pickle with the protein materials. However, during this resting period the TGase which is added to the pickle, crosslinks and polymerizes the protein contained in the pickle thereby increasing the viscosity of the resulting pickle solution. This increase in viscosity makes subsequent use of the pickle difficult and if the method of producing the meat involves injection, makes the procedure almost impossible to conduct. There have been several attempts to modify the pickle containing TGase to avoid the increased viscosity.

Japanese Patent Application Laid-open Nos. 255426/1995 and 56303/1999 report techniques for suppressing the increase of pickle viscosity caused by TGase. The techniques involve controlling the quantities of caseins and soy bean protein which are highly reactive with TGase or using protein partial hydrolysates. These techniques suppress the viscosity increase with no influence on TGase activity, by reducing the effective TGase substrate concentration or by using proteins that are less susceptible to TGase action, e.g., protein partial hydrolysates. However, when the protein component of the pickle is changed the original purposes of the protein, such as imparting physical properties and water-holding capacity to the processed meat products, are significantly lower compared with the original types of proteins. This results in the undesirable property of poor elasticity and significant water release from the resulting product. When protein partial hydrolysates are used, the viscosity can be maintained for approximately one day, but is often not sufficiently suppressed during a longer term of storage. Since caseins and soy bean protein are used only in the form of their partial hydrolysates, the creation of diverse food taste, food texture and/or quality based on devised blending of various protein materials is greatly restricted. Thus, pickles containing TGase are limited when the TGase is used with lower amounts of protein. In addition, the pickles must be used within one day and the remaining unused portion is discarded.

SUMMARY OF THE INVENTION

On the background of the conventional techniques described above, it is an object of the present invention to provide a salting agent without any of the aforementioned disadvantages even after the salting agent is blended with TGase and with no need of any modification or treatment of protein materials added to the pickle.

The present inventors have investigated a solution to the aforementioned problems and have found to suppress the reaction by TGase in a pickle is accomplished by adding a TGase suppressing compound. This results in the ability to regulate TGase activity and allows maintenance of a low viscosity pickle. Thus, the present invention has been achieved.

The invention is essentially different from the conventional techniques by controlling the TGase activity whereby TGase can be added to pickle without modification to the preferable compounds of the pickle which would otherwise not be possible.

The present invention further provides a salting agent for meat processing, which comprises TGase and a compound which suppresses TGase activity; a pickle containing the salting agent; methods of making a processed meat using the salting agent and/or pickle; and the processed meats so obtained.

DETAILED DESCRIPTION OF THE INVENTION

TGases are divided into calcium-independent and calcium-dependent types. Either can be used in the present invention. Examples of the former include those derived from microorganisms such as Actinomycete, Bacillus subtilis and the like (see, for example, JP-A-64-27471). Examples of the latter include those derived from guinea pig liver (see, for example, JP-B-1-50382), those derived from microorganisms such as Oomycetes, those derived from animals such as bovine blood, swine blood and the like, those derived from fish such as salmon, red sea bream and the like (see, for example, Seki Nobuo et al., Nippon Suisan Gakkaishi, vol. 56, pp. 125–132 (1990), and Proceedings of Nippon Fisheries Science Association, Congress in Spring, 1990, page 219), Factor XIII present in blood (WO 93/15234), those derived from oysters, and other TGases. Also, TGases produced by methods of genetic engineering (see, for example, JP-A-1-300889, JP-A-6-225775, JP-A-7-23737 and EP-0693556A) can be used in the present invention. In accordance with the present invention, any of these TGases can be used, with no specific limitation of the origin and the preparation method. However, in view of the function and the economics in the food applications the calcium-independent TGases are preferable. For example, the TGases derived from the microorganisms (JP-A-64-27471 mentioned above) meet all conditions, and are preferred.

The terms "suppress", "suppression", and "suppressing" as used within the present specification and claims are understood to mean any reduction of TGase activity in the presence of the TGase suppressing compound compared to the TGase activity in the absence of the same compound. It is further understood that the level of "suppression" will vary depending on the amount of TGase present and the concentration of the suppressing compound. The compound which can suppress TGase activity includes those which can reversibly inhibit TGase. Examples of such compounds include inorganic or organic ammonium salts. Preferably, inorganic ammonium salts are used. Examples of such inorganic ammonium salts include ammonium chloride, ammonium carbonate, ammonium hydrogen carbonate, ammonium aluminum sulfate, ammonium persulfate, ammonium sulfate, diammonium hydrogen phosphate, and ammonium dihydrogen phosphate. Organic ammonium salts include for example ammonium citrate. Anserine, carnosine and balenine, which can control certain physical properties of surimi (fish paste) products can also be used as the suppressing compound. The compounds can be used singly or in combination of two or more.

The suppressing compound is selected based on the kind of the protein used and the amount of TGase added to the pickle because each compound has its own ability to suppress TGase activity based on the total weight of the protein. Preferably, ammonium chloride is used because it is commonly used as a seasoning, as a baking powder in premix, is approved as an enzyme stabilizer, and because it is very inexpensive.

When TGase suppression is within a pickle, the amount of the compound added to the pickle may be high. The compound is added in an amount suitable to inhibit TGase activity to such an extent that the increase of the viscosity of the resulting pickle is sufficiently suppressed but not to substantially reduce the effect of TGase in the final food product because after introduction into the meat, the effective concentration of the suppressing compound is less and thus has a lower suppression effect. The optimum amount of the suppressing compound may vary, depending on the amount of TGase added, suppressing effect of the suppressing compound, the protein composition in the pickle used, the level of viscosity suppression required, and the overall conditions for the meat production.

The amount of the suppressing compound is in an amount greater than 0.001 mol/liter, preferably greater than 0.002 mol/liter, which is suitable to suppress TGase activity and pickle viscosity. When ammonium salt is used as the suppressing compound, if the concentration exceeds 0.2 mol/liter, the requisite TGase activity in the meat product is not attained. Therefore, when ammonium salts are used as the suppressing compound, the ammonium salt concentration is preferably below 0.1 mol/liter.

The amount of TGase to be added to pickle varies depending on the pickle injection ratio, and the level of TGase activity which is required. Generally, TGase is used at a concentration within a range of 20 U to 1,000 U/liter in a pickle. This includes 40, 60, 80, 100, 150, 250, 300, 400, 500, 600, 700, 800, 900 and all values and subranges there between.

The activity of TGase and the activity units thereof can be assayed and defined by the following method. More specifically, TGase activity is tested in a reaction containing the substrates benzyloxycarbonyl-L-glutamylglycine and hydroxylamine in Tris buffer, pH 6.0, at a temperature of 37° C.; where the hydroxamic acid formed is modified into an iron complex in the presence of trichloroacetic acid. The absorbance of this reaction is measured at 525 nm and the amount of hydroxamic acid formed is calculated from a standard curve. The enzyme producing 1 μmol hydroxamic acid per minute is defined as one unit (1 U) of TGase activity (see Japanese Patent Laid-open No. 27471/1989 and U.S. Pat. No. 5,156,956; the entire contents of which are incorporated herein by reference).

Because the preparation according to the present invention is an enzyme preparation of TGase with an ammonium salt in mixture, the ratio of the ammonium salt and TGase blended in the enzyme preparation is within a range simultaneously satisfying the individual concentrations when added to a pickle. For example, 20 U/liter of TGase blended with 0.2 mol/liter of an ammonium salt in pickle corresponds to a 10 moles of ammonium salts per 1,000 U of TGase in the preparation; and 1,000 U/liter of TGase blended with 0.001 mol/liter of an ammonium salt in the pickle corresponds to 0.001 mole of ammonium salts per 1,000 U TGase in the preparation. Thus, the enzyme preparation according to the present invention contains at least these two ingredients, the ammonium salt being blended from 0.001 mole to 10 moles, preferably 0.002 mole to 5 moles, per 1,000 U of TGase. When shown in terms of the weight ration to TGase, the ammonium salt is in an amount of from 0.02 mole to 200 moles, preferably 0.04 mole to 100 moles per gram of the pure enzyme protein.

Any type of protein materials generally employed in pickles can be used. Examples of such proteins include soy bean protein, caseins, egg white, whey protein, gelatin, collagen and plasma protein because the proteins themselves doe not result in an increased pickle viscosity.

To make a pickle solution, the composition contains TGasae and TGase suppressing compound is dissolved in cold water along with protein materials and sodium chloride which is generally used. Following the initial dissolution stage of making the pickle solution, the pickle solution contains foam which deteriorates the quality of the final product. Therefore, the foam can be removed by vacuum or by leaving the pickle in cold storage for at least one night. The pickle solution can then be injected into the raw meat material using a pickle injector as is known in the art. The pickle can also be introduced into the pcike by immersing the raw meat material in the pickle. Afterwards, the meat is tumbled and the pickle is dispersed uniformly in the meat.

The application of the composition of TGase and TGase suppressing compound according to the present invention is not limited to the manufacture of meat products. The composition can also be used in the general applications other than meat products in which a solution comprising TGase and protein materials is injected into raw food materials.

Having generally described this invention, a further understanding can be obtained by reference to certain specific examples which are provided herein for purposes of illustration only, and are not intended to be limiting unless otherwise specified.

EXAMPLES

"Activa TG" (1,000 U/g; manufactured by Ajinomoto, Co. containing as the major ingredient TGase derived from genus Streptoverticillium (Streptoverticillium mobaraense IFO 13819) was used as the TGase in the examples.

Example 1

Effects of TGase Suppressing Compound on the Viscosity of a Pickle Containing TGase and the Assessment of a Processed Meat Using the Pickle A stock pickle solution of the composition shown in Table 1 was prepared by the following process. Water cooled at 5° C. was put into a mixing chamber and the protein materials were dissolved and mixed, followed by the other ingredients listed in the table. To the stock pickle solution "Activa TG" was added to the pickle in the final concentrations of: (1) 0%; (2) 0.005%; (3) 0.010%; (4) 0.015%; or (5) 0.020% as shown in Table 2. In separate preparations the amount of "Activa TG" added was fixed at 0.020% and ammonium chloride was added to the following concentrations: (6) 0.002 mol/liter; (7) 0.02 mol/liter: and (8) 0.2 mol/liter (Table 2).

TABLE 1

Pickle solution

| Ingredients | Concentration (%) |
| --- | --- |
| Soy bean protein for ham | 4 |
| Sodium casein | 1.5 |
| Egg white | 2 |
| Whey protein | 1.5 |
| Sodium chloride | 4 |
| Sodium nitrite | 0.03 |
| Polymerized phosphate (salt) | 0.6 |
| Ascorbic acid | 0.2 |
| Dextrin | 7.5 |
| Sugar | 0.7 |
| Glutamate Na | 0.3 |
| Water | 77.67 |
| Total | 100 |

TABLE 2

TGase and TGase suppressing compounds in pickle solutions

| Experimental groups | TGase (U/liter) | NH$_4$Cl (mol/liter) | Anserine (mol/liter) | Carnosine (mol/liter) |
| --- | --- | --- | --- | --- |
| (1) | 0 | 0 | — | — |
| (2) | 50 | 0 | — | — |
| (3) | 100 | 0 | — | — |
| (4) | 150 | 0 | — | — |
| (5) | 200 | 0 | — | — |
| (6) | 200 | 0.002 | — | — |
| (7) | 200 | 0.02 | — | — |
| (8) | 200 | 0.2 | — | — |
| (9) | 200 | — | 0.2 | — |
| (10) | 200 | — | — | 0.2 |

The pickle samples were left to stand in a low-temperature chamber at 5° C.; and the viscosity was measured over time. The change of the pickle viscosity over time was measured with a Type B viscometer with a No. 2 rotor at 30 rpm.

In separate tests, 100 parts of each pickle samples after one day were added to 100 parts of minced meat prepared by finely chopping and cutting pork loin through a 5-mm-sieve plate; mixing with a Stefan cutter for 3 minutes and filling in a fibrous casing (φ 90 mm). The ham was dried and aged in a smoke chamber at 60° C. for 120 minutes, then smoked at 60° C. for 60 minutes, and finally steam boiled at 75° C. for 120 minutes. The breaking strength of the model ham was measured with a plunger of φ 5 mm at 6 cm/min. The quality of the ham was also assessed. The results are collectively shown in Table 3.

TABLE 3

Pickle viscosity, physical properties and quality assessment of the model ham

| Experimental groups | Pickle viscosity (cP) at 5° C. | | | | Breaking strength of the model ham (gram) | Quality assessment of the model ham* |
| --- | --- | --- | --- | --- | --- | --- |
| | Immediately after preparation | one day later | 2 days later | 3 days later | | |
| (1) | 29 | 30 | 32 | 34 | 537 | X |
| (2) | 31 | 35 | 41 | 83 | 599 | X |
| (3) | 30 | 94 | 125 | 444 | 680 | Δ |
| (4) | 32 | 74 | 153 | 808 | 733 | ○ |
| (5) | 27 | 114 | 317 | 3855 | 773 | ○ |
| (6) | 26 | 52 | 110 | 312 | 770 | ○ |
| (7) | 31 | 44 | 66 | 95 | 752 | ○ |
| (8) | 30 | 31 | 36 | 45 | 686 | Δ |
| (9) | 31 | 41 | 58 | 87 | 722 | ○ |
| (10) | 31 | 42 | 56 | 90 | 734 | ○ |

*: Effect of the TGase on firmness of the ham
X: insufficient;
Δ: slightly insufficient; and
○: sufficient.

Pickle Viscosity:

There was little change in viscosity when no TGase was added to the pickle (group (1)). However, as the amount of added "Activa TG" increased, the pickle viscosity also increased (Experimental groups (2) to (5)). In particular, noting in Experimental group (5), which contains 0.02% "Activa TG", the viscosity was above 3,000 cP on day 3. This pickle could not be used in the preparation of meat products. In contrast, the increase of the viscosity was significantly suppressed in the ammonium chloride groups (Experimental groups (6) to (8)). Additionally, the viscosity increased less as the amount of ammonium chloride was added increased and similarly in the pickle solutions having anserine (Experimental Group (9)) and Carnosine (Experimental Group (10)).

Breaking Strength of the Model Ham

The break strength of the model ham increased as the amount of "Activa TG" increased, indicating the enhancement of the firmness and elasticity as food taste and texture (see Experimental group (5)). In contrast, the break strength slightly decreased in the ammonium chloride groups as the amount of ammonium chloride was increased (Experimental groups (6) to (8)). However, in relation to positive effects gained in pickle viscosity the decrease in break strength is not considered to be significant. Similar results were obtained when anserine and carnosine were used (Experimental groups (9) and (10)). These results indicated that while the TGase activity was inhibited in the pickle, the TGase activity was restored upon addition to the ham.

Example 2

Preparation of Salting Agent for Meat Products

One existing enzyme preparation and three enzyme preparations for meat products in accordance with the present invention were prepared according to the recipes A, B, C and D in Table 4. "Activa TG" was used as the TGase; and ammoniuni chloride commercially available as a food additive was used.

TABLE 4

| Preparations | Salting agent | | | |
|---|---|---|---|---|
| | Activa TG* (gram) | NH$_4$Cl (gram) | Lactose (gram) | Total (gram) |
| A | 10 | 0 | 90 | 100 |
| B | 10 | 5.25 | 84.75 | 100 |
| C | 10 | 52.5 | 37.5 | 100 |
| D | 1 | 52.5 | 45.5 | 100 |

*1 gram Activa TG corresponds to 1,000 U TGase activity/g.

To the pickle of the composition made in Example 1 (Table 1), the preparations in Table 4 were added in the following amounts: (1) No addition; (2) Preparation A at 0.2%; (3) Preparation B at 0.2%; (4) Preparation C at 0.2%; and (5) Preparation D at 2.0%. The TGase concentration was constant in all the experimental groups (2) to (5). The change of the viscosity of the pickle was measured over time. The viscosity results are shown in Table 5.

Roast ham was prepared concurrently with these pickle samples one day after making the pickle. The roast ham was prepared from a raw pork loin in a conventional manner.

The pickle was injected into pork loin using a pickle injector. The pickle injection ratio was 100% by weight to the raw material meat, and then tumbling was carried out overnight at 5° C. The tumbled meat was filled in a fibrous casing with a folding width of 11 cm and was cooked. Cooking conditions were 60° C. for 2 hours for drying, 60° C. for 1 hour for smoking, and 75° C. for 2 hours for steam boiling. The ham was sliced into pieces of 2-mm thickness. The food taste and texture were evaluated and the results are shown in Table 6.

TABLE 5

| | | | Pickle viscosity | | | | | |
|---|---|---|---|---|---|---|---|---|
| | | Amount added to pickle | Concentrate in pickle | | Pickle viscosity in cP at 5° C. | | | |
| Experimental groups | Preparations | | TGase in U/liter | NH$_4$Cl in mol/liter | Immediately after preparation | one day later | 2 days later | 3 days later |
| 1 | — | — | 0 | 0 | 32 | 32 | 33 | 32 |
| 2 | A | 0.2% | 200 | 0 | 33 | 130 | 358 | 4500 |
| 3 | B | 0.2% | 200 | 0.002 | 34 | 66 | 131 | 364 |
| 4 | C | 0.2% | 200 | 0.02 | 30 | 46 | 71 | 102 |
| 5 | D | 2.0% | 200 | 0.2 | 29 | 33 | 38 | 54 |

TABLE 6

Sensory evaluation of roast ham

| Experimental groups | | Quality assessment* |
|---|---|---|
| (1) | Soft with insufficient firmness | X |
| (2) | Good firmness | ○ |
| (3) | Good firmness at the same level as in (2) | ○ |
| (4) | Good firmness at the same level as in (2) | ○ |

TABLE 6-continued

Sensory evaluation of roast ham

| Experimental groups | | Quality assessment* |
|---|---|---|
| (5) | Slightly softer than (2) but with sufficient firmness | Δ–○ |

*Effect of the TG on firmness
X: insufficient;
Δ: slightly poor; and
○: sufficient/Good.

Pickle Viscosity:

The viscosity increase in the pickle of group (2) with the addition of the Preparation A with no content of ammonium chloride was very rapid. In contrast, the viscosity increase was remarkably suppressed in the pickle of groups (3), (4) and (5) with the addition of the Preparations B, C and D, respectively, each containing ammonium chloride. Furthermore, a higher viscosity suppression was observed in Preparation C which contained a higher concentration of ammonium chloride. Compared with the no addition group (1), the effect of TGase on the physical properties of ham was almost at the same level in the three experimental groups (2), (3) and (4). Compared with the group (2), the group (5) was slightly less firm, but the preparation of the group (5) sometimes serves as an effective blend for when no increase in pickle viscosity can be tolerated.

Advantages of the Invention

When a composition for food processing which contains TGase and a compound suppressing TGase activity is used in pickle, the increase in the viscosity of the pickle can be markedly suppressed, with little or no influence on the action of TGase and the resulting taste and texture of the final food product.

The present application is based on the Japanese priority application JP 263479 filed Sep. 17, 1999, which is herein incorporated in its entirety by reference.

Obviously, numerous modifications and variations on the present invention are possible in light of the above teachings. It is therefore to be understood that within the scope of the appended claims, the invention may be practiced otherwise than as specifically described herein.

What is claimed is:

1. A pickle solution comprising at least one protein, at least one transglutaminase, an ammonium salt in an amount of from 0.001 mol/liter to 0.02 mol/liter, and water.

2. A method of making a processed meat comprising adding the pickle solution of claim 1 to a meat.

3. The method of claim 2, wherein said adding comprises immersing the meat into said pickle solution.

4. The method of claim 2, wherein said adding comprises injecting said pickle into said meat.

5. The pickle solution of claim 1, wherein said ammonium salt is selected from the group consisting of ammonium chloride, ammonium carbonate, ammonium hydrogen carbonate, ammonium aluminum sulfate, ammonium iron citrate, ammonium persulfate, ammonium sulfate, diammonium hydrogen phosphate and ammonium dihydrogen phosphate.

6. A method of making the pickle solution of claim 5, comprising:

mixing the protein, and from 0.001 mol/liter to 0.02 mol/liter ammonium salt in water; and adding the transglutaminse.

7. The method of claim 6, wherein after said adding, the pickle solution is stored for a period of one to four days.

8. A method of making a processed meat comprising adding the pickle solution of claim 5 to a meat.

9. The method of claim 8, wherein said adding comprises immersing the meat into said pickle solution.

10. The method of claim 8, wherein said adding comprises injecting said pickle into said meat.

11. The pickle solution of claim 1, wherein said ammonium salt is ammonium chloride.

12. A method of making the pickle solution of claim 11, comprising:

mixing the protein, and from 0.001 mol/liter to 0.02 mol/liter ammonium salt in water; and adding the transglutaminse.

13. The method of claim 12, wherein after said adding, the pickle solution is stored for a period of one to four days.

14. A method of making a processed meat comprising adding the pickle solution of claim 11 to a meat.

15. The method of claim 14, wherein said adding comprises immersing the meat into said pickle solution.

16. The method of claim 14, wherein said adding comprises injecting said pickle into said meat.

17. The pickle solution of claim 1, wherein said protein is selected from the group consisting of soybean protein, casein, egg white protein, whey protein, gelatin, collagen and plasma protein.

18. A method of making the pickle solution of claim 17, comprising:

mixing the protein, and from 0.001 mol/liter to 0.02 mol/liter ammonium salt in water; and adding the transglutaminse.

19. The method of claim 18, wherein after said adding, the pickle solution is stored for a period of one to four days.

20. A method of making a processed meat comprising adding the pickle solution of claim 17 to a meat.

21. The method of claim 20, wherein said adding comprises immersing the meat into said pickle solution.

22. The method of claim 20, wherein said adding comprises injecting said pickle into said meat.

23. A method of making the pickle solution of claim 1, comprising:

mixing the protein, and from 0.001 mol/liter to 0.02 mol/liter ammonium salt in water; and adding the transglutaminse.

24. The method of claim 23, wherein after said adding, the pickle solution is stored for a period of one to four days.

\* \* \* \* \*